United States Patent
Fremy et al.

(10) Patent No.: US 11,434,513 B2
(45) Date of Patent: *Sep. 6, 2022

(54) METHOD FOR PRODUCING MERCAPTANS BY DISULFIDE ENZYME HYDROGENOLYSIS

(71) Applicant: ARKEMA FRANCE, Colombes (FR)

(72) Inventors: Georges Fremy, Sauveterre de Bearn (FR); Arnaud Masselin, Saint Malo (FR)

(73) Assignee: ARKEMA FRANCE, Colombes (FR)

( * ) Notice: Subject to any disclaimer, the term of this patent is extended or adjusted under 35 U.S.C. 154(b) by 126 days.

This patent is subject to a terminal disclaimer.

(21) Appl. No.: 15/764,480

(22) PCT Filed: Sep. 29, 2016

(86) PCT No.: PCT/FR2016/052479
§ 371 (c)(1),
(2) Date: Mar. 29, 2018

(87) PCT Pub. No.: WO2017/055752
PCT Pub. Date: Apr. 6, 2017

(65) Prior Publication Data
US 2019/0055586 A1 Feb. 21, 2019

(30) Foreign Application Priority Data
Sep. 30, 2015 (FR) ...................... 1559257

(51) Int. Cl.
*C12P 11/00* (2006.01)
*C12N 9/02* (2006.01)
*C07C 319/06* (2006.01)

(52) U.S. Cl.
CPC ............ *C12P 11/00* (2013.01); *C07C 319/06* (2013.01); *C12N 9/0036* (2013.01); *C12N 9/0051* (2013.01); *C12Y 101/9901* (2013.01); *C12Y 108/00* (2013.01)

(58) Field of Classification Search
CPC ..... C12P 11/00; C12N 9/0036; C12N 9/0051; C12Y 108/00; C12Y 101/9901; C07C 319/06; C07C 321/04
See application file for complete search history.

(56) References Cited

U.S. PATENT DOCUMENTS

| | | | |
|---|---|---|---|
| 4,059,638 A | 11/1977 | Kubicek | |
| 4,657,856 A | 4/1987 | Terada et al. | |
| 5,493,058 A | 2/1996 | Cadot et al. | |
| 7,759,523 B2 | 7/2010 | Redlingshöfer et al. | |
| 8,008,530 B2 | 8/2011 | Redlingshöfer et al. | |
| 8,426,648 B2 | 4/2013 | Barre et al. | |
| 9,562,006 B2 | 2/2017 | Fremy | |
| 10,563,236 B2 * | 2/2020 | Fremy | ........... C12Y 108/01007 |
| 10,648,007 B2 * | 5/2020 | Fremy | ........... C12Y 108/01007 |
| 2005/0260250 A1 | 11/2005 | Ott | |
| 2007/0015941 A1 | 1/2007 | Brand et al. | |
| 2007/0213564 A1 | 9/2007 | Yang et al. | |
| 2008/0293974 A1 | 11/2008 | Barth et al. | |
| 2009/0054691 A1 | 2/2009 | Redlingshofer et al. | |
| 2010/0094059 A1 | 4/2010 | Yang et al. | |
| 2010/0236448 A1 | 11/2010 | Yang et al. | |
| 2011/0015443 A1 | 1/2011 | Barth et al. | |
| 2018/0273991 A1 | 9/2018 | Fremy et al. | |

FOREIGN PATENT DOCUMENTS

| | | |
|---|---|---|
| CN | 103053703 A | 4/2013 |
| EP | 0649837 A1 | 4/1995 |
| JP | H07304730 A | 11/1995 |
| JP | 2018529356 A | 10/2018 |
| RU | 2408577 C2 | 1/2011 |
| WO | 0196290 A1 | 12/2001 |
| WO | 2004096760 A1 | 11/2004 |
| WO | 2005107723 A2 | 11/2005 |
| WO | 2006015668 A1 | 2/2006 |
| WO | 2007028708 A1 | 3/2007 |
| WO | 2008118925 A2 | 10/2008 |
| WO | 2010046607 A1 | 4/2010 |
| WO | 2013092129 A1 | 6/2013 |
| WO | 2014033399 A1 | 3/2014 |

OTHER PUBLICATIONS

C. Neumann et al. "Nicotinamide adenine dinucleotide phosphateregenerating system coupled to a glutathione-reductasen microtiter method for determination of total glutathione concentrations in adherent growing cancer cell lines", Analytical Biochemistry 320(2): 170-178 (Year: 2003).*
F. Honda. "Studies on Thiamine 8-(Methyl 6-Acetyl-Dihydrothioctate) Disulfide [Thiamine 8-(Methyl 6-acetyldihydrothioctate) Disulfide", Vitamins (Japan), vol. 36 No. 5 459-465. (provided with English translation) (Year: 1967).*
Chemical Book entry for Octotiamine, retrieved from https://www.chemicalbook.com/ChemicalProductProperty_EN_CB9365412.htm on Oct. 7, 2020 (Year: 2017).*
Bolten et al, Towards Methionine Overproduction in Corynebacterium glutamicum—Methanethiol and Dimethyldisulfide as Reduced Sulfur Sources. J. Microbiol. Biotechnol., 2010, vol. 20(8): 1196-1203. (Year: 2010).*
Calvin M., Mercaptans and Disulfides: Some Physics, Chemistry, and Speculation. Lawrence Berkeley National Laboratory, 1954, pp. 1-44. (Year: 1954).*
Gregory et al., Metabolism of Sulfur Compounds (Sulfate Metabolism). Annu. Rev. Biochem., 1960, vol. 29: 347-364. (Year: 1960).*
McGorrin RJ., The Significance of Volatile Sulfur Compounds in Food Flavors An Overview .Chapter 1, 2011, American Chemical Society, pp. 1-29. (Year: 2011).*
Toohey et al., Thiosulfoxide (Sulfane) Sulfur: New Chemistry and New Regulatory Roles in Biology. Molecules, 2014, vol. 19: 12789-12813. (Year: 2014).*

(Continued)

*Primary Examiner* — Ganapathirama Raghu
(74) *Attorney, Agent, or Firm* — RatnerPrestia

(57) ABSTRACT

Provided is an enzymatic process for preparing mercaptans from disulfides.

10 Claims, 1 Drawing Sheet

(56) References Cited

OTHER PUBLICATIONS

Du et al., "Derivation of Oridonin with Bioreduction-Responsive Disulfide Bond", Chinese Journal of Chemistry, vol. 32, No. 5, May 22, 2014, pp. 448-453.
International Search Report and Written Opinion for International Application No. PCT/FR2016/052479 dated Jan. 17, 2017—12 pages.
Keire et al., "Kinetics and Equilibria of Thiol/disulfide Interchange Reactions of Selected Biological Thiols and Related Molecules with Oxidized Glutathione", The Journal of Organic Chemistry, vol. 57, No. 1, Jan. 1992, pp. 123-127.
Lui et al., "Oligomeric Hydrogels Self-Assembled from Reduction-Controlled Condensation", Angwe. Chemie International Edition, vol. 54, No. 12, Mar. 16, 2015, pp. 3639-3642.
Millis et al., "Oxidation/reduction potential of Glutathione", The Journal of Organic Chemistry, American Chemical Society, vol. 58, No. 15, Jan. 1993, pp. 4144-4146.
Stewart et al., "Mycothiol Disulfide Reductase: Solid Phase Synthesis and Evaluation of Alternative Substrate Analogues", Organic & Biomolecular Chemistry, vol. 6, No. 2, Jan. 2008, p. 385.
Szajewski et al., "Rate Constants and Equilibrium Constants for Thiol-disulfide Interchange Reactions Involving Oxidized Glutathione", Journal of the American Chemical Society, American Chemical Society, vol. 102, No. 6, Mar. 1980, pp. 2011-2025.
Van Dijken et al., "Novel Pathway for Alcoholic Fermentation of δ-Gluconolactane in the Yeast *Saccaromyces bulderi*", Journal of Bacteriology, Feb. 2002, pp. 672-678.
Chandrawati, R., et al., "Triggered Cargo Release by Encapsulated Enzymatic Catalysis in Capsosomes", Nano Letters, 11:4958-4963, (2011), pubs.acs.org/NanoLett.

\* cited by examiner

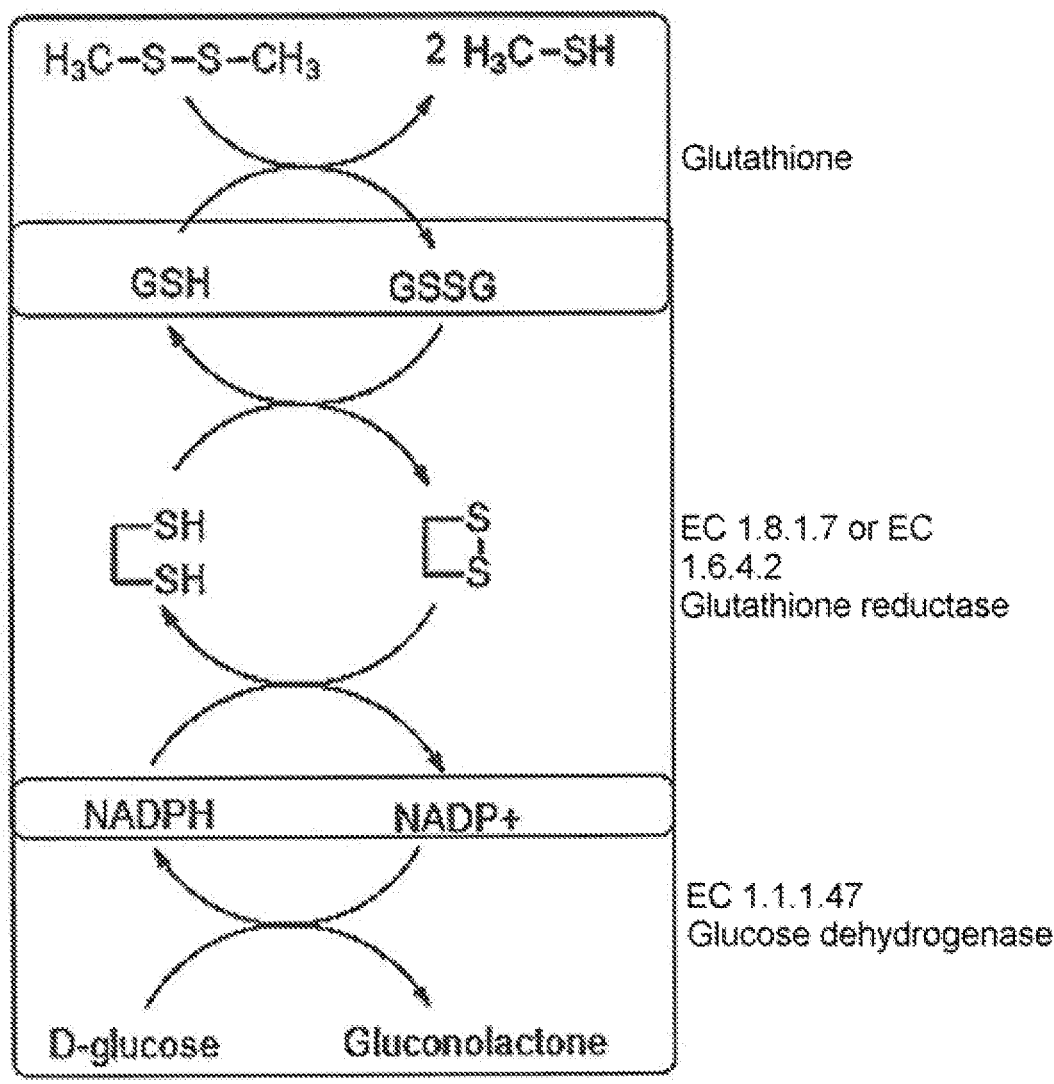

METHOD FOR PRODUCING MERCAPTANS BY DISULFIDE ENZYME HYDROGENOLYSIS

CROSS-REFERENCE TO RELATED APPLICATIONS

This is the national phase of International Application No, PCT/FR2016/052479, filed 29 Sep. 2016, which claims priority to French Application No. 1559257, filed 30 Sep. 2015. The disclosure of each of these applications is incorporated herein by reference in its entirety for all purposes.

FIELD OF THE INVENTION

The present invention relates to a process for the production by enzymatic catalysis of mercaptans, in particular of methyl mercaptan, from disulfides, in particular dimethyl disulfides, and using organic reducing compounds.

BACKGROUND OF THE INVENTION

Mercaptans are highly useful in very numerous fields, for example as flavourings, odorants for gases, chain transfer agents in polymerisation, starting materials for the pharmaceutical or cosmetic industry, for the synthesis of antioxidants, extreme-pressure or anti-wear additives for lubrication. These examples do not in any way limit the uses of the mercaptans known at present and which can be prepared by virtue of the process of the invention.

In particular, the first of the mercaptans, methyl mercaptan ($CH_3SH$), is very industrially beneficial, in particular as starting material in the synthesis of methionine, an essential amino acid very widely used in animal feed. Methyl mercaptan is also a starting material very widely used for the synthesis of numerous other molecules.

Mercaptans may be synthesised by numerous methods such as the sulfhydration of alcohols, the catalytic or photochemical addition of hydrogen sulfide onto unsaturated organic compounds, the substitution of halides, epoxides or organic carbonates by means of hydrogen sulfide, and others.

In particular, methyl mercaptan is currently produced industrially on the tonne scale from methanol and hydrogen sulfide according to the reaction (1):

$$CH_3OH + H_2S \rightarrow CH_3SH + H_2O \quad (1)$$

These processes have the drawbacks of requiring methanol ($CH_3OH$), of synthesising hydrogen sulfide ($H_2S$, from hydrogen and sulfur for example, which also then requires the synthesis of hydrogen), and give rise to by-products of dimethyl ether ($CH_3OCH_3$), dimethyl sulfide ($CH_3SCH_3$) type, and products of cracking and water, which implies numerous steps for purification of the methyl mercaptan.

By way of examples, the description of processes based on these reactions will be found in patent applications such as WO2013092129, WO2008118925, WO2007028708, WO2006015668 and WO2004096760.

It may prove economically advantageous (to avoid methanol synthesis) to wish to produce methyl mercaptan from carbon monoxide, hydrogen and hydrogen sulfide, according to the following synthesis scheme (2):

$$CO + 2H_2 + H_2S \rightarrow CH_3SH + H_2O \quad (2)$$

However, these processes have the drawbacks of requiring synthesis gas ($CO/H_2$) and therefore carrying out steam reforming of a source of hydrocarbons, having the correct proportions between CO and $H_2$, hence being able to adjust the $CO/H_2$ ratio with what is referred to as the "water-gas shift reaction" ($CO + H_2O \rightarrow CO_2 + H_2$), and synthesising $H_2S$.

These processes also generally lead to large proportions of $CO_2$ as by-product, and also to methane, dimethyl sulfide and water. By way of example, descriptions of these processes will be found in patent applications US2010286448, US2010094059, US2008293974, US2007213564.

Yet other processes have been described, and combine different reactions such as:

1) Formation of $CS_2$ and $H_2S$ from methane and sulfur (3):

$$CH_4 + 4S \rightarrow CS_2 + 2H_2S \quad (3)$$

2) Hydrogenation of $CS_2$ (4):

$$CS_2 + 3H_2 \rightarrow CH_3SH + H_2S \quad (4)$$

It is also possible to use the excess $H_2S$ from reactions (3) and (4) in the reaction with methanol (reaction 1) or the reaction with synthesis gas (reaction 2) to further give methyl mercaptan.

These processes obviously combine the drawbacks described for reactions (1) and (2) with the additional difficulty of having excess hydrogen to carry out reaction (4). Descriptions of these processes will be found in patent applications US2011015443, or, more specifically in relation to reaction (4), in application WO2010046607.

Application WO200196290 proposes a process for synthesising methyl mercaptan directly from methane and $H_2S$ with coproduction of hydrogen. This direct reaction between methane and $H_2S$ occurs by means of a pulsed plasma with corona discharge. Since this application does not describe any examples of synthesis, it may appear difficult to imagine a process for the large-scale industrial synthesis of methyl mercaptan with this technology. Moreover, this process requires the synthesis of $H_2S$ if the latter is not available.

For its part, patent application EP0649837 proposes a process for the synthesis of methyl mercaptan by catalytic hydrogenolysis, with transition metal sulfides, of dimethyl disulfide with hydrogen. Although this process is efficient, it requires relatively high temperatures of the order of 200° C. to obtain industrially advantageous levels of productivity.

Those skilled in the art also know that it is possible to prepare methyl mercaptan by acidification of an aqueous solution of sodium methyl mercaptide ($CH_3SNa$). This method has the major drawback of producing large amounts of salts, such as sodium chloride or sodium sulfate, depending on whether hydrochloric acid or sulfuric acid is used. These saline aqueous solutions are often very difficult to treat and the traces of foul-smelling products which remain mean that this method cannot be readily envisaged on the industrial scale.

The processes for synthesising mercaptans higher than methyl mercaptan also have numerous drawbacks. Thus, the substitution of alcohols with hydrogen sulfide requires high temperatures, and often pressures, and leads to undesired by-products of olefin, ether and sulfide type.

The catalytic or photochemical addition of hydrogen sulfide onto unsaturated compounds often occurs under slightly milder conditions than above, but also leads to numerous by-products formed by isomerisation of the starting material, by non-regioselective addition or by double addition which gives sulfides. Finally, the substitution of halogenated derivatives gives rise to processes which generate large amounts of effluents and saline waste which are not easily reconcilable with industrial processes.

SUMMARY OF THE INVENTION

The subject of the present invention is to propose a novel process for preparing mercaptans, in particular methyl mercaptan, which does not have the drawbacks described in the processes known from the prior art laid out above.

More particularly, a first subject-matter of the present invention is the process for the preparation of a mercaptan of formula R—SH, comprising at least the steps of:
a) preparation of a mixture comprising:
  1) a disulfide of formula R—S—S—R',
  2) a catalytic amount of amino acid bearing a thiol group or of a thiol-group-containing peptide,
  3) a catalytic amount of an enzyme catalysing the reduction of the disulfide bridge created between two equivalents of said amino acid bearing a thiol group or of said thiol-group-containing peptide,
  4) a catalytic amount of an enzyme catalysing the dehydrogenation of the organic reducing compound involved in step b),
  5) a catalytic amount of a cofactor common to the two enzymes catalysing the reduction and the dehydrogenation,
b) addition of an organic reducing compound in a stoichiometric amount relative to the disulfide of formula R—S—S—R',
c) carrying out the enzymatic reaction,
d) recovery of the mercaptan of formula R—SH and of the mercaptan of formula R'—SH,
e) separation and optional purification of the mercaptan of formula R—SH and of the mercaptan of formula R'—SH.

BRIEF DESCRIPTION OF THE FIGURE

FIGURE: Reduction with the glutathione/glutathione reductase complex.

DETAILED DESCRIPTION OF THE INVENTION

Generally speaking, the enzyme catalysing the reduction of the disulfide bridge created between two equivalents of said amino acid bearing a thiol group or said thiol-group-containing peptide is a reductase enzyme. The term "reductase" is used in the remainder of the description for explaining the present invention. Similarly, the enzyme catalysing the dehydrogenation of the organic reducing compound involved in step b) is generally referred to as a dehydrogenase enzyme, the term "dehydrogenase" being chosen in the remainder of the description for explaining the present invention.

Among the cofactors common to the two enzymes catalysing the reduction and the dehydrogenation (reductase and dehydrogenase), mention may be made, by way of non-limiting examples, of flavinic cofactors and nicotinic cofactors. Preference is given to using nicotinic cofactors and more particularly nicotinamide adenine dinucleotide (NAD), or better still nicotinamide adenine dinucleotide phosphate (NADPH). The cofactors listed above are advantageously used in their reduced forms (for example NADPH, H+) and/or their oxidized forms (for example NADP+), that is to say that they may be added in these reduced and/or oxidized forms into the reaction medium.

In one embodiment of the invention, the amino acid bearing a thiol group and/or the thiol-group-containing peptide may be in the form of the disulfide of said amino acid and/or of said peptide, respectively, for example glutathione in the form of glutathione disulfide.

The organisation and the order of the additions of the different components of steps a) and b) of the process defined above may be carried out in different ways. In any case, the enzymatic reaction of step c) is triggered by the addition of one of the components of the catalytic system: either an enzyme, or one of the compounds added in a stoichiometric amount (disulfide or organic reducing compound), or one of the compounds added in a catalytic amount (amino acid bearing a thiol group or thiol-group-containing peptide or disulfide corresponding to said molecules or else the cofactor).

Even more particularly, a subject-matter of the present invention is the process for the preparation of a mercaptan of formula R—SH, comprising at least the steps of:
a') preparation of a mixture comprising:
  a disulfide of formula R—S—S—R',
  a catalytic amount of amino acid bearing a thiol group or of a thiol-group-containing peptide,
  a catalytic amount of reductase enzyme corresponding to said amino acid bearing a thiol group or to said thiol-group-containing peptide,
  a catalytic amount of NADPH,
b') addition of an organic reducing compound in a stoichiometric amount relative to the disulfide and DMDS) with a catalytic amount of the corresponding dehydrogenase enzyme,
c') carrying out the enzymatic reaction,
d') recovery of the mercaptan of formula R—SH and of the mercaptan of formula R'—SH,
e') separation and optional purification of the mercaptan of formula R—SH and of the mercaptan of formula R'—SH.

Within the context of the present invention, any disulfide corresponding to the general formula R—S—S—R' may be involved in the process for producing mercaptan. In the general formula R—S—S—R', R and R', which are identical or different, represent independently of one another a linear, branched or cyclic hydrocarbon-based radical comprising from 1 to 20 carbon atoms, said chain being saturated or bearing one or more unsaturations in the form of double or triple bond(s). R and R' may also form together, and with the sulfur atoms bearing them, a cyclic molecule comprising from 4 to 22 atoms, preferably from 5 to 10 atoms.

According to a preferred aspect, the radicals R and R', which are identical or different, are chosen independently of one another from linear or branched, saturated or unsaturated alkyl, cycloalkyl, aryl, alkylaryl or arylalkyl radicals comprising from 1 to 20 carbon atoms, preferably from 1 to 12 carbon atoms, more preferably still from 1 to 6 carbon atoms and optionally functionalised by one or more functions chosen, nonlimitingly and by way of example, from alcohol, aldehyde, ketone, acid, amide, nitrile or ester functions or else functions bearing sulfur, phosphorus, silicon or halogen.

The disulfide of formula R—S—S—R' is able to be reduced, according to the process of the invention, to mercaptan of formula R—SH and mercaptan of formula R'—SH. When R is different to R', reference is made to asymmetrical disulfides, and when R and R' are identical, reference is made to symmetrical disulfides. In the case of symmetrical disulfides R—S—S—R, the process of the invention leads to a mercaptan of formula R—SH. According to a particularly preferred aspect of the invention, dimethyl disulfide (DMDS) is used with the aim of producing methyl mercaptan $CH_3SH$.

In the case of asymmetrical disulfides R—S—S—R', the process of the invention leads to a mixture of mercaptans of formulae R—SH and R'—SH, which may either be used as is or else subjected to one or more separation operations well known to those skilled in the art, for example distillation.

It is also possible to use, in the process of the invention, mixtures of one or more symmetrical and/or asymmetrical disulfides. Possible mixtures of disulfides may comprise DSOs (disulfide oils), said DSOs thus finding a highly advantageous possibility of exploitation.

According to the process of the invention, the mercaptan(s) produced are generally recovered in the form of a solid, a liquid and/or a gas.

The production process according to the invention is based on the enzymatic reduction of disulfides, in particular dimethyl disulfide, with an organic reducing compound, which is a hydrogen donor as will be defined below, according to the following reaction, illustrated with dimethyl disulfide leading to methyl mercaptan, using glucose as organic reducing compound (hydrogen donor):

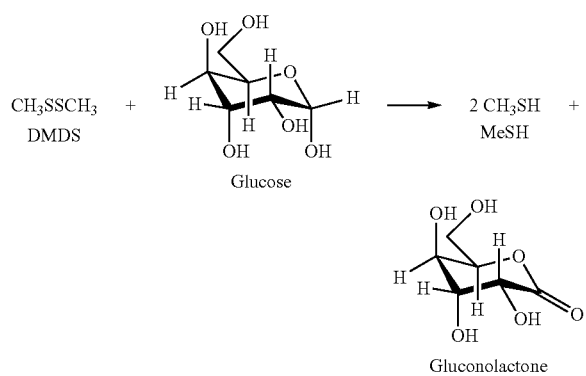

It has now been discovered that this reaction is readily catalysed by the enzymatic system employing a thiol-group-containing amino acid or a thiol-group-containing peptide, for example glutathione, in the form of an (amino acid or peptide)/corresponding reductase enzyme complex, regenerated by the hydrogen-donating organic compound, as described in the appended FIG. 1.

Thus, according to the illustration in FIG. 1, the peptide (the example represented being glutathione) reduces the disulfide (DMDS represented) to mercaptan (methyl mercaptan represented) by converting into a peptide with a disulfide bridge (glutathione disulfide represented). The reductase enzyme (glutathione reductase represented, enzyme classification numbers EC 1.8.1.7 or EC 1.6.4.2) regenerates the peptide (glutathione) and this same enzyme is regenerated by a redox enzymatic complex well known to those skilled in the art, for example the NADPH/NADP+ (nicotinamide adenine dinucleotide phosphate (reduced form and oxidized form)) complex. NADP+ is in turn regenerated to NADPH by means of the dehydrogenase enzyme corresponding to the organic reducing compound used (here, glucose dehydrogenase, EC 1.1.1.47) by virtue of said organic reducing compound (glucose represented) which provides hydrogen (hydrogen donor) by converting to its oxidized form (here, gluconolactone).

In other words, the enzyme catalysing the reaction (glutathione reductase represented with the example enzyme classification numbers EC 1.8.1.7 or EC 1.6.4.2) regenerates the peptide (glutathione) while oxidizing the cofactor (NADPH,H+ represented). The oxidized form (NADP+ represented) is then reduced by means of a "recycling" redox enzymatic complex well known to those skilled in the art and comprising the dehydrogenase enzyme involved (glucose dehydrogenase represented with the example enzyme classification number EC 1.1.1.47) and the organic reducing molecule (glucose represented). The oxidized form of the organic reducing compound is then obtained (gluconolactone represented).

According to a most particularly suited embodiment, the glutathione/glutathione disulfide system combined with the glutathione reductase enzyme makes it possible according to the present invention to reduced the DMDS to methyl mercaptan.

Glutathione is a tripeptide widely used in biology. In reduced form (glutathione) or oxidized form (glutathione disulfide), this species forms an important redox couple in cells. Thus, glutathione is vital for eliminating heavy metals from organisms. Thus, for example, application WO05107723 describes a formulation in which glutathione is used to form a chelating preparation and U.S. Pat. No. 4,657,856 teaches that glutathione also makes it possible to break down peroxides such as $H_2O_2$ into $H_2O$ via glutathione peroxidase. Finally, glutathione also makes it possible to reduce disulfide bridges present in proteins (Rona Chandrawati, "Triggered Cargo Release by Encapsulated Enzymatic Catalysis in Capsosomes", *Nano Lett.*, (2011), vol. 11, 4958-4963).

According to the process of the invention, a catalytic amount of amino acid bearing a thiol group or of a thiol-group-containing peptide is used to produce mercaptans from disulfides.

Among the amino acids bearing a thiol group which may be used in the process of the present invention, mention may be made by way of nonlimiting examples of cysteine and homocysteine. In these cases, the redox enzymatic systems used which can regenerate the catalytic cycle in the same way as the system cysteine/cystine reductase EC 1.8.1.6 and homocysteine/homocysteine reductase.

Among the peptides bearing a thiol group which may be used in the process of the present invention, mention may be made by way of nonlimiting examples of glutathione and thioredoxin. The glutathione/glutathione reductase system described above may thus be replaced by the thioredoxin (CAS No. 52500-60-4)/thioredoxin reductase (EC 1.8.1.9 or EC 1.6.4.5) system.

Glutathione and the glutathione/glutathione reductase system are most particularly preferred for the present invention, due to the costs of these compounds and the ease with which they are procured.

Among the organic reducing compounds which may be used within the context of the present invention, hydrogen-donating compounds are most particularly preferred, and among these, the entirely suitable compounds are hydrogen-donating organic reducing compounds bearing a hydroxyl function, such as alcohols, polyols, sugars, etc.

The enzyme used is an enzyme able to dehydrogenate the hydrogen-bearing compound, for example an alcohol dehydrogenase. Glucose is a most particularly well-suited sugar to be used in the process of the present invention with glucose dehydrogenase to give gluconolactone.

In the process according to the invention, only the disulfide(s) and the glucose are used in a stoichiometric amount and all the other components (amino acid or peptide, cofactor (for example NADPH) and the 2 enzymes) are used in catalytic amounts.

The advantages brought about by the process of the invention are numerous. Among these advantages, mention may be made of the possibility of working in aqueous or aqueous-organic solution, under very mild temperature and pressure conditions and under pH conditions close to neutrality. All these conditions are typical of a "green" or "sustainable" biocatalytic process.

Another advantage when the process uses dimethyl disulfide is that the methyl mercaptan produced, which is in the gaseous state under the reaction conditions, leaves the reaction medium as it is formed. The methyl mercaptan may therefore be directly used, upon leaving the reactor, in an application further downstream. It can also be readily liquefied cryogenically for example, if it is desired to isolate it. It is optionally possible to accelerate its departure from the reaction medium by introducing a low flow rate of nitrogen, by bubbling.

The dimethyl disulfide (DMDS) may be produced at another site from methyl mercaptan and an oxidizer such as oxygen, sulfur or aqueous hydrogen peroxide solution, for example, or else from dimethyl sulfate and sodium disulfide. The DMDS may also originate from a source of disulfide oils (DSO), as indicated above, then be purified for example by reactive distillation as described in application WO2014033399. It should be noted that the DSOs may also be used as is, without the necessity for purification between the different disulfides composing them. A mixture of mercaptans is then obtained by applying the process of the invention.

When DMDS is used as disulfide, the process according to the invention is can then be considered as a process which makes it possible to avoid transporting methyl mercaptan from its site of production by existing industrial routes, to its site of use, if they are different. Indeed, methyl mercaptan is a toxic and extremely foul-smelling gas at room temperature, which significantly complicates its transportation, which is already heavily regulated unlike DMDS. The process described in the present invention can therefore be used to produce methyl mercaptan directly on the site of use of the latter.

Since the DMDS is consumed in the reaction and the methyl mercaptan leaves the reaction medium as it is formed, only the product of the dehydrogenation of the organic reducing compound, for example gluconolactone, accumulates in the reaction medium, if it is assumed that glucose and DMDS are fed continuously. When the gluconolactone concentration exceeds the saturation point under the reaction conditions, it will precipitate out and may then be isolated from the reaction medium by any means known to those skilled in the art.

Gluconolactone may have several uses. It is for example used as a food additive, known by the reference E575. Gluconolactone is hydrolysed in acidic aqueous media to form gluconic acid, also used as a food additive (E574). Gluconolactone is also used for the production of tofu (cf. CN 103053703) for the food industry.

Especially and advantageously, in the sense that it represents the "waste" from the process according to the present invention, gluconolactone may replace glucose in a possible fermentation reaction to produce either bioethanol or any other molecule originating from the fermentation of sugar or starch.

Indeed, certain bacteria may use gluconolactone as carbon source in fermentation, as described by J. P. van Dijken, *"Novel pathway for alcoholic fermentation of gluconolactone in the yeast Saccharomyces bulderi"*, J. Bacteriol., (2002), Vol. 184(3), 672-678.

Yet other sugars may be used in the process of the invention, and for example it is possible to replace the glucose/gluconolactone/glucose dehydrogenase system with the following system: glucose 6-phosphate/6-phosphoglucono-δ-lactone/glucose6-phosphate dehydrogenase (EC 1.1.1.49).

It is also possible, in the process of the invention, to use an alcohol in place of the sugar, and thus to use the following general system instead of the glucose/gluconolactone/glucose dehydrogenase system: alcohol/ketone or aldehyde/alcohol dehydrogenase (EC 1.1.1) and more particularly the isopropanol/acetone/isopropanol dehydrogenase system (EC 1.1.1.80).

Indeed, this system makes it possible to obtain, when DMDS is used as disulfide, a mixture consisting of methyl mercaptan (MeSH) and acetone which leaves the reaction medium (therefore no accumulation of any product). The MeSH and the acetone may be easily separated by simple distillation if desired. In the case of other disulfides, depending on the boiling point of the mercaptan formed and its solubility in the reaction medium, the acetone may be readily removed from the medium and the mercaptan may optionally settle out of the reaction medium, in order to be easily separated.

Generally, the reaction temperature is within a range extending from 10° C. to 50° C., preferably between 15° C. and 45° C., more preferably between 20° C. and 40° C.

The pH of the reaction may be between 6 and 8, preferably between 6.5 and 7.5. The pH of the reaction medium may be adjusted by means of a buffer. Entirely preferably, the pH of the phosphate buffer will be chosen to be 7.3.

The pressure used for the reaction may range from a reduced pressure compared to atmospheric pressure to several bar (several hundred kPa), depending on the reagents and equipment used. In the case where DMDS is used as disulfide, a reduced pressure may indeed enable quicker degassing of the methyl mercaptan formed, but has the drawback of increasing the saturated vapour pressures of the water and the DMDS, polluting the methyl mercaptan formed slightly more. Preferably, use will be made of a pressure ranging from atmospheric pressure to 20 bar (2 MPa) and even more preferably the process will be carried out under a pressure ranging from atmospheric pressure to 3 bar (300 kPa).

The process according to the invention can be carried out batchwise or continuously, in a glass or metal reactor depending on the operating conditions selected and the reagents used.

The ideal organic reducing compound/disufide molar ratio is stoichiometry (molar ratio=1) but may vary from 0.01 to 100, if those skilled in the art find any benefit therein, such as continuous addition of disulfide while the reducing compound is introduced from the start into the reactor. Preferably, this molar ratio is chosen between 0.5 and 5 overall, over the whole of the reaction.

The elements present in catalytic amounts in the mixture prepared in step a) above (amino acid bearing a thiol group or a thiol-group-containing peptide, reductase enzyme, cofactor such as, for example, NADPH) are easily available commercially or can be prepared according to techniques well known to those skilled in the art. These different elements may be in solid or liquid form and may very advantageously be dissolved in water to be used in the process of the invention. The enzymes used may also be grafted onto a support (in the case of supported enzymes).

The aqueous solution of enzymatic complex comprising the amino acid or the peptide may also be reconstituted by methods known to those skilled in the art, for example by permeabilization of cells which contain these elements. This aqueous solution, a composition of which is given in the following Example 1, may be used in contents by weight of between 0.01% and 20% relative to the total weight of the reaction medium. Preferably, a content of between 0.5% and 10% will be used.

According to another aspect, the present invention relates to the use of an aqueous solution of enzymatic complex comprising an amino acid bearing a thiol function as defined above or a peptide bearing a thiol function as defined above, for the synthesis of a mercaptan from a disulfide.

The mixture which can be used for step a) of the process described above and comprising:
1) a disulfide of formula R—S—S—R',
2) a catalytic amount of amino acid bearing a thiol group or a thiol-group-containing peptide,
3) a catalytic amount of an enzyme catalysing the reduction of the disulfide bridge created between two equivalents of said amino acid bearing a thiol group or to said thiol-group-containing peptide,
4) optionally a catalytic amount of an enzyme catalysing the dehydrogenation of an organic reducing compound,
5) a catalytic amount of a cofactor common to the two enzymes catalysing the reduction and the dehydrogenation, where R and R' are as defined above,
is novel and hence is part of the present invention.

In one embodiment of the invention, the amino acid bearing a thiol group and/or the peptide bearing a thiol group can be in the form of the disulfide of said amino acid and/or of said peptide, respectively.

More particularly, said mixture comprises:
a disulfide of formula R—S—S—R',
a catalytic amount of amino acid bearing a thiol group or a thiol-group-containing peptide,
a catalytic amount of reductase enzyme corresponding to said amino acid bearing a thiol group or to said thiol-group-containing peptide, and
a catalytic amount of NADPH,
where R and R' are as defined above.

The invention will be better understood with the following examples nonlimiting relative to the scope of the invention.

EXAMPLES

Example 1

10 ml of glutathione enzymatic complex (Aldrich) and 19.2 g (0.1 mol) of glucose are introduced into a reactor containing 150 ml of 0.1 mol/l phosphate buffer at pH 7.30. The solution of enzymatic complex contains: 185 mg (0.6 mmol) of glutathione, 200 U of glutathione reductase, 50 mg (0.06 mmol) of NADPH and 200 U of glucose dehydrogenase. The reaction medium is brought to 25° C. with mechanical stirring. A first sample is taken at t=0. Subsequently, the dimethyl disulfide (9.4 g, 0.1 mol) is placed in a burette and added dropwise to the reactor; the reaction begins. A stream of nitrogen is placed in the reactor. Gas chromatography analysis of the gases leaving the reactor shows virtually essentially the presence of nitrogen and methyl mercaptan (some traces of water). These outlet gases are trapped in 20% sodium hydroxide in water. The DMDS is introduced in 6 hours and the reaction is monitored by potentiometric argentometric titration of the methyl mercaptan sodium salt in the trap at the outlet of the reactor. In addition, a final gas chromatography analysis of the reaction medium confirms the absence of DMDS, and by UPLC/mass spectrometry traces of glucose and the virtually exclusive presence of gluconolactone are found.

Example 2

To the reaction medium of Example 1, 19.2 g (0.1 mol) of glucose are reintroduced in one go, and 9.4 g (0.1 mol) of DMDS are reintroduced dropwise in 6 hours. The reaction is monitored in the same way as in Example 1, after having changed the 20% sodium hydroxide solution at the outlet of the reactor. The analyses at the end of the reaction confirm the complete disappearance of the DMDS, totally converted into methyl mercaptan found in sodium salt form in the sodium hydroxide solution. Only the gluconolactone is analysed and found in the reaction medium at the end of the reaction. This example shows the robustness of the catalytic system through its reproducibility.

The invention claimed is:
1. A process for the preparation of a mercaptan of formula R—SH, consisting of:
(a) preparing a mixture, comprising:
(1) a disulfide of formula R—S—S—R',
wherein R and R', independently, represent a linear, branched or cyclic hydrocarbon-based radical comprising from 1 to 20 carbon atoms, wherein the hydrocarbon-based radical is saturated,
(2) an amino acid bearing a thiol group or of a thiol-group-containing peptide, wherein the amino acid bearing a thiol group or the thiol-group-containing peptide may optionally be in the form of the corresponding disulfide,
(3) an enzyme catalyzing the reduction of a disulfide bridge created between two equivalents of the amino acid bearing a thiol group or the thiol-group-containing peptide,
(4) an enzyme catalyzing dehydrogenation of an organic reducing compound,
(5) a cofactor common to the enzyme from (a)(3) catalyzing the reduction and the enzyme from (a)(4) catalyzing the dehydrogenation,
(b) adding the organic reducing compound from (a)(4),
(c) carrying out the enzymatic reaction,
(d) recovering the mercaptan of formula R—SH and the mercaptan of formula R'—SH,
(e) optionally, separating and, optionally, purifying the mercaptan of formula R—SH and/or the mercaptan of formula R'—SH;
wherein the amino acid bearing a thiol group is chosen from cysteine, homocysteine, glutathione and thioredoxin,
wherein the enzyme catalyzing the reduction of a disulfide bridge created between two equivalents of the amino acid bearing a thiol group or the thiol group-containing peptide is chosen from cysteine reductase, glutathione reductase and thioredoxin reductase,
wherein the cofactor is a nicotinic cofactor,
wherein the organic reducing compound is chosen from glucose, glucose 6-phosphate, and isopropanol, and
wherein the enzyme catalyzing dehydrogenation of the organic reducing compound is chosen from the glucose dehydrogenase, the glucose 6-phosphate dehydrogenase, the isopropanol dehydrogenase system.

2. The process of claim 1, consisting of:
(a') preparing a mixture, comprising:
the disulfide of formula R—S—S—R',
the amino acid bearing a thiol group or of a thiol-group-containing peptide,
the enzyme catalyzing the reduction of a disulfide bridge created between two equivalents of the amino acid bearing a thiol group or the thiol-group-containing peptide,
the enzyme catalyzing dehydrogenation of an organic reducing compound, and
a cofactor common to the enzyme catalyzing the reduction and the enzyme catalyzing the dehydrogenation, where the cofactor is NADPH,
(b') adding the organic reducing compound,
(c') carrying out the enzymatic reaction,
(d') recovering the mercaptan of formula R—SH and the mercaptan of formula R'—SH,
(e') separating and, optionally, purifying the mercaptan of formula R—SH and the mercaptan of formula R'—SH.

3. The process of claim 1, wherein the disulfide of formula R—S—S—R' is dimethyl disulfide.

4. The process of claim 1, wherein the pH of the reaction is between 6 and 8.

5. The process of claim 1, wherein the pH of the reaction is between 6.5 and 7.5.

6. The process of claim 1, wherein the organic reducing compound/disulfide molar ratio is between 0.01 and 100 over the whole of the reaction.

7. The process of claim 1, wherein the organic reducing compound/disulfide molar ratio is between 0.5 and 5 over the whole of the reaction.

8. The process of claim 1, wherein the amino acid bearing a thiol group or a thiol-group-containing peptide is glutathione.

9. The process of claim 1, wherein
the disulfide of formula R—S—S—R' is dimethyl disulfide (DMDS), and
the amino acid bearing a thiol group or the peptide bearing a thiol group is glutathione.

10. The process of claim 1, wherein
the disulfide of formula R—S—S—R' is dimethyl disulfide (DMDS),
the amino acid bearing a thiol group or the peptide bearing a thiol group is glutathione,
the organic reducing compound is glucose, and
the cofactor is NADPH.

* * * * *